United States Patent [19]
De Castro

[11] Patent Number: 5,534,270
[45] Date of Patent: Jul. 9, 1996

[54] METHOD OF PREPARING STABLE DRUG NANOPARTICLES

[75] Inventor: Lan De Castro, West Chester, Pa.

[73] Assignee: NanoSystems LLC, Collegeville, Pa.

[21] Appl. No.: 386,028

[22] Filed: Feb. 9, 1995

[51] Int. Cl.$^6$ .......................................................... A61K 9/14

[52] U.S. Cl. .......................... 424/490; 424/489; 424/494; 424/497

[58] Field of Search ..................................... 424/489, 490, 424/494, 497

[56] References Cited

U.S. PATENT DOCUMENTS 5,399,363  3/1995  Liversidge .............................. 424/490
5,488,133  1/1996  Singh et al. ........................... 424/9.45

*Primary Examiner*—Jeffrey Mullis
*Attorney, Agent, or Firm*—Rudman & Balogh

[57] ABSTRACT

Stable dispersible particles consisting essentially of a crystalline drug substance having a surface modifier adsorbed on the surface thereof in an amount sufficient to maintain an effective average particle size of less than about 400 nm are prepared by providing a drug substance, depyrogenating grinding media, mixing the drug substance, grinding media and autoclaving and adding a surface modifier either during autoclaving or after autoclaving and subsequently wet milling. Pharmaceutical compositions containing the particles exhibit unexpected bioavailability and are useful in methods of treating mammals.

14 Claims, No Drawings

METHOD OF PREPARING STABLE DRUG NANOPARTICLES

FIELD OF THE INVENTION

This invention relates to methods for the preparation of stable drug particles. This invention further relates to the use of such particles in pharmaceutical compositions and methods of treating mammals.

BACKGROUND OF INVENTION

Bioavailability is the degree to which a drug becomes available to the target tissue after administration. Many factors can affect bioavailability including the dosage form and various properties, e.g., dissolution rate of the drug. Poor bioavailability is a significant problem encountered in the development of pharmaceutical compositions, particularly those containing an active ingredient that is poorly soluble in water. Poorly water soluble drugs, i.e., those having a solubility less than about 10 mg/ml, tend to be eliminated from the gastrointestinal tract before being absorbed into the circulation. Moreover, poorly water soluble drugs tend to be unsafe for intravenous administration techniques, which are used primarily in conjunction with fully soluble drug substances.

It is know that the rate of dissolution of a particulate drug can increase with increasing surface area, i.e., decreasing particle size. Consequently, methods of making finely divided drugs have been studied and efforts have been made to control the size and size range of drug particles in pharmaceutical compositions. For example, dry milling techniques have been used to reduce particle size and hence influence drug absorption. However, in conventional dry milling, as discussed by Lachman, et al., *The Theory and Practice of Industrial Pharmacy*, Chapter 2, "Milling", p.45, (1986), the limit of fineness is reached in the region of 100 microns (100,000 nm) when material cakes on the milling chamber. Lachman, et al, note that wet grinding is beneficial in further reducing particle size, but that flocculation restricts the lower particle size limit to approximately 10 microns (10,000 nm). However, there tends to be a bias in the pharmaceutical art against wet milling due to concerns associated with contamination. Commercial airier milling techniques have provided particles ranging in average particle size from as low as about 1 to 50 µm (1,000–50,000 nm).

Other techniques for preparing pharmaceutical compositions include loading drugs into liposomes or polymers, e.g., during emulsion polymerization. However, such techniques have problems and limitations. For example, a lipid soluble drug is often required in preparing suitable liposomes. Further, unacceptably large amounts of the liposomes or polymer are often required to prepare unit drug doses. Further still, techniques for preparing pharmaceutical compositions tend to be complex. A principal technical difficulty encountered with emulsion polymerization is the removal of contaminants, such as unreacted monomer or initiator, which can be toxic, at the end of the manufacturing process.

U.S. Pat. No. 4,540,602 (Motoyama et al.) discloses a solid drug pulverized in an aqueous solution of a water soluble high molecular substance using a wet grinding machine. However, Motoyama et al. teach that as a result of such wet grinding, the drug is formed into finely divided particles ranging from 0.5 µm (500 nm) or less to 5 µm (5,000 nm) in diameter.

EPO 275,796 describes the production of collidally dispersible systems comprising a substance in the form of spherical particles smaller than 500 nm. However, the method involves a precipitation effected by mixing a solution of the substance and a miscible non-solvent for the substance and results in the formation of non-crystalline nanoparticle. Furthermore, precipitation techniques for preparing particles tend to provide particles contaminated with solvents. Such solvents are often toxic and can be very difficult, if not impossible, to adequately remove to pharmaceutically acceptable levels to be practical.

U.S. Pat. No. 4,107,288 describes particles in the size range from 10 to 1,000 nm containing a biologically or pharmacodynamically active material. However, the particles comprise a crosslinked matrix of macromolecules having the active material supported on, or incorporated into, the matrix.

U.S. Pat. No. 5,145,684 describes a method of providing stable, dispersible nanoparticulate drugs in the submicron size range which are formed by wet milling poorly soluble drugs in conjunction with a surface modifier.

The nanoparticulate drugs have been found to be quite stable to flocculation or agglomeration, particularly when the grinding media is depyrogenated and the grinding media and drug are wet milled in a liquid milling medium and thereafter autoclaved and the surface modifier is added.

It would be desirable to provide nanoparticulate drugs which exhibit even further enhanced stability against agglomeration to achieve enhanced bioavailability.

SUMMARY OF THE INVENTION

I have discovered a method of preparing stable, dispersible drug nanoparticles by providing drug particles, depyrogenating grinding media and mixing the drug particles and grinding media and autoclaving prior to adding a surface modifier and wet milling the drug substance sufficient to maintain an effective particle size of less than 400 nm. It is quite surprising that the autoclaving procedure prior to milling the drug substance not only did not result in eventual agglomeration of the drug nanoparticles, but actually further stabilized the drug nanoparticle.

In another embodiment of this invention, an alternative method of preparing stable, dispersible drug nanoparticles comprises providing a drug substance, depyrogenating grinding media, mixing the drug substance and grinding media with surface modifier and autoclaving followed by wet grinding the autoclaved drug substance to maintain an effective particle size of less than 400 nm.

It is an advantageous feature that a wide variety of surface modified drug nanoparticles free of unacceptable contamination can be prepared in accordance with this invention.

It is another advantageous feature of this invention that there is provided a simple and convenient method for preparing drug nanoparticles by wet milling in conjunction with a surface modifier.

Another particularly advantageous feature of this invention is that pharmaceutical compositions are provided which are expected to exhibit high bioavailability.

Still another advantageous feature of this invention is that pharmaceutical compositions containing poorly water soluble drug substances are provided which are suitable for intravenous administration techniques.

Other advantageous features will become readily apparent upon reference to the following Description of Preferred Embodiments.

DESCRIPTION OF PREFERRED EMBODIMENTS

This invention is based on the preparation of stabilized nanoparticulate crystalline drug particles by:

1) providing a drug substance having a solubility in water of less than 10 mg/ml,
2) depyrogenating rigid grinding media,
3) mixing the drug substance and grinding media and autoclaving and
4) adding a surface modifier to the autoclaved drug substance and grinding media in a dispersion medium and wet grinding the drug substance sufficient to maintain an effective average particle size of less than 400 nm.

The particles of this invention comprise a drug substance. The drug substance exists as a discrete, crystalline phase. The crystalline phase differs from a non-crystalline or amorphous phase which results from precipitation techniques, such as described in EPO 275,796 cited above.

The invention can be practiced with a wide variety of drug substances. The drug substance preferably is present in an essentially pure form. The drug substance must be poorly soluble and dispersible in at least one liquid medium. By "poorly soluble" it is meant that the drug substance has a solubility in the liquid dispersion medium of less than about 10 mg/ml, and preferably of less than about 1 mg/ml. A preferred liquid dispersion medium is water. However, the invention can be practiced with other liquid media in which a drug substance is poorly soluble and dispersible including, for example, aqueous salt solutions, safflower oil and solvents such as ethanol, t-butanol, hexane and glycol. The pH of the aqueous dispersion media can be adjusted by techniques known in the art.

Suitable drug substances can be selected from a variety of known classes of drugs including, for example, analgesics, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardia inotropic agents, contrast media, corticosteroids, cough suppressants (expectorants and mucolytics), diagnostic agents, diagnostic imaging agents, diuretics, dopaminergics (antiparkinsonian agents), haemostatics, immuriological agents, lipid regulating agents, muscle relaxants, parasympathomimetics, parathyroid calcitonin and bisphosphonates, prostaglandins, radio-pharmaceuticals, sex hormones (including steroids), anti-allergic agents, stimulants and anorectics, sympathomimetics, thyroid agents, vasodilators and xanthines. Preferred drug substances include those intended for oral administration and intravenous administration. A description of these classes of drugs and a listing of species within each class can be found in Martindale, The Extra Pharmacopoeia, Twenty-ninth Edition, The Pharmaceutical Press, London, 1989, the disclosure of which is hereby incorporated by reference in its entirety. The drug substances are commercially available and/or can be prepared by techniques known in the art.

Representative illustrative species of drug substances useful in the practice of this invention include:

17-α-pregno-2,4-dien-20-yno-[2,3-d]-isoxazol-17-ol (Danazol);

5α,17α,-1'(methylsulfonyl)-1'-H-pregn-20-yno[3,2 -c]-pyrazol-17-ol (Steroid A);

piposulfam;

piposulfan;

phenytoin;

camptothecin; and ethyl-3,5-diacetoamido-2,4,6-triiodobenzoate.

In particularly preferred embodiments of the invention, the drug substance is Phenytoin.

The particles of this invention can be prepared in a method comprising the steps of dispersing a drug substance in a liquid dispersion medium and applying mechanical means in the presence of grinding media to reduce the particle size of the drug substance to an effective average particle size of less than about 400 nm. The particles can be reduced in size in the presence of a surface modifier. Alternatively, the particles can be contacted with a surface modifier after attrition.

A general procedure for preparing the particles of this invention is set forth below. The drug substance selected is obtained commercially and/or prepared by techniques known in the art in a conventional coarse form. It is preferred, but not essential, that the particle size of the coarse drug substance selected be less than about 100 μm as determined by sieve analysis. If the coarse particle size of the drug substance is greater than about 100 μm, then it is preferred that the particles of the drug substance be reduced in size to less than 100 μm using a conventional milling method such as airjet or fragmentation milling.

In step 2 of the process, the grinding media for the milling procedure is depyrogenated.

The grinding media for the particle size reduction step can be selected from rigid media preferably spherical or particulate in form having an average size less than about 3 mm and, more preferably, less than about 1 mm. such media desirably can provide the particles of the invention with shorter processing times and impart less wear to the milling equipment. The selection of material for the grinding media is not believed to be critical. It has been found that zirconium oxide, such as 95% ZrO stabilized with magnesia, zirconium silicate, and glass grinding media provide particles having levels of contamination which are believed to be acceptable for the preparation of pharmaceutical compositions. However, other media, such as stainless steel, titania, alumina, and! 95% ZrO stabilized with yttrium, are expected to be useful. Preferred media have a density greater than about 3 g/cm$^3$.

The depyrogenation process involves putting the grinding media in an ovens to destroy any bacteria or pyrogens in the media. The media is generally washed first in deionized water and dried. The depyrogenation is carried out by pouring the grinding media beads into a bottle covered with aluminum foil and placing in an oven for from 6 to 20 hours, preferably 8 and at temperatures of 200° to 300° C., preferably 240° C. to 260° C. This procedure is done outside the presence of the drug substance as the high temperature may alter the characteristics of the drug material and may well cause the final drug nanoparticles to agglomerate prior to use.

In the third step of this process, the drug substance and rigid grinding media are autoclaved to prevent the drug substance from bacteria infection and agglomeration. The autoclaving process is carried out by starting at room temperature in an autoclave pouch and autoclaving, at from 100° to 150° C. for a period of from 10 to 60 minutes. It is preferred to autoclave at about 121° C. for about 20 minutes.

In step four, a surface modifier is added to the autoclaved drug substance and rigid grinding media and the drug substance is subjected to wet grinding sufficient to maintain an effective average particle size of less than 400 nm.

The particles of this invention contain a discrete phase of a drug substance as described above having a surface modifier adsorbed on the surface thereof. Useful surface modifiers are believed to include those which physically adhere to the surface of the drug substance but do not chemically bond to the drug.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants. Representative examples of excipients include gelatin, casein, lecithin (phosphatides), gum acacia, cholesterol, tragacanth, stearic acid, benzalkonium chloride, calcium stearate, glyceryl monostearate, cestostearl alcohol, cetamacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, and polyvinylpyrrolidone (PVP). Most of these excipients are described in detail in the Handbook of Pharmaceutical Excipients, published jointly by the American Pharmaceutical Association and The Pharmaceutical Society of Great Britain, The Pharmaceutical Press 1986, the disclosure of which is hereby incorporated by reference in its entirety. The surface modifiers are commercially available and/or can be prepared by techniques known in the art.

Particularly preferred surface modifiers include polyvinylpyrrolidone, Pluronic F68 and F108, which are block copolymers of ethylene oxide and propylene oxide, Tetronic 908, which is a tetrafunctional block copolymer derived from sequential addition of ethylene oxide and propylene oxide to ethylenediamine, dextran, lecithin, Aerosol OT, which is a dioctyl ester of sodium sulfosuccinic acid, available from American Cyanamid, Duponol P, which is a sodium lauryl sulfate, available from DuPont, Triton X-200, which is an alkyl aryl polyether sulfonate available from Rohm and Haas, Tween 80, which is a polyoxyethylene sorbitan fatty acid ester, available from ICI Specialty Chemicals, and Carbowax 3350 and 934, which are polyethylene glycols available from Union Carbide. Surface modifiers which have found to be particularly useful include polyvinylpyrrolidone, Pluronic F-68, and lecithin.

The surface modifier is adsorbed on the surface of the drug substance in an amount sufficient to maintain an effective average particle size of less than about 400 nm. The surface modifier does not chemically react with the drug substance or itself. Furthermore, the individually adsorbed molecules of the surface modifier are essentially free of intermolecular crosslinkages.

As used herein, particle size refers to a number average particle size as measured by conventional particle size measuring techniques well known to those skilled in the art, such as sedimentation field flow fractionation, photon correlation spectroscopy, or disk centrifugation. By "an effective average particle size of less than about 400 nm" it is meant that at least 90% of the particles have a weight average particle size of less than about 400 nm when measured by the above-noted techniques. In preferred embodiments of the invention, the effective average particle size is less than about 250 nm. In some embodiments of the invention, an effective average particle size of less than about 100 nm has been achieved. With reference to the effective average particle size, it is preferred that at least 95% and, more preferably, at least 99% of the particles have a particle size less than the effective average, e.g., 400 nm. In particularly preferred embodiments, essentially all of the particles have a size less than 400 nm. In some embodiments, essentially all of the particles have a size less than 250 nm.

The particles of this invention can be prepared in a method comprising the steps of dispersing a drug substance in a liquid dispersion medium and applying mechanical means in the presence of grinding media to reduce the particle size of the drug substance to an effective average particle size of less than about 400 nm. The particles can be reduced in size in the presence of a surface modifier. Alternatively, the particles can be contacted with a surface modifier after attrition.

A general procedure for preparing the particles of this invention is set forth below. The drug substance selected is obtained commercially and/or prepared by techniques known in the art in a conventional coarse form. It is preferred, but not essential, that the particle size of the coarse drug substance selected be less than about 100 μm as determined by sieve analysis. If the coarse particle size of the drug substance is greater than about 100 μm, then it is preferred that the particles of the drug substance be reduced in size to less than 100 μm using a conventional milling method such as airjet or fragmentation milling.

The coarse drug substance selected can then be added to a liquid medium in which it is essentially insoluble to form a premix. The concentration of the drug substance in the liquid medium can vary from about 0.1–60%, and preferably is from 5–30% (w/w). It is preferred, but not essential, that the surface modifier be present in the premix. The concentration of the surface modifier can vary from about 0.1 to about 90%, and preferably is 1–75%, more preferably 20–60%, by weight based on the total combined weight of the drug substance and surface modifier. The apparent viscosity of the premix suspension is preferably less than about 1000 centipoise.

The premix can be used directly by subjecting it to mechanical means to reduce the average particle size in the dispersion to less than 400 nm. it is preferred that the premix be used directly when a ball mill is used for attrition. Alternatively, the drug substance and, optionally, the surface modifier, can be dispersed in the liquid medium using suitable agitation, e.g., a roller mill or a Cowles type mixer, until a homogenous dispersion is observed in which there are no large agglomerates visible to the naked eye. It is preferred that the premix be subjected to such a premilling dispersion step when a recirculating media mill is used for attrition.

The mechanical means applied to reduce the particle size of the drug substance conveniently can take the form of a dispersion mill. Suitable dispersion mills include a ball mill, an attritor mill, a vibratory mill, and media mills such as a sand mill and a bead mill. A media mill is preferred due to the relatively shorter milling time required to provide the intended result, i.e., the desired reduction in particle size. For media milling, the apparent viscosity of the premix preferably is from about 100 to about 1000 centipoise. For ball milling, the apparent viscosity of the premix preferably is from about 1 up to about 100 centipoise. Such ranges tend to afford an optimal balance between efficient particle fragmentation and media erosion.

The surface modifier, if it was not present in the premix, must be added to the dispersion after attrition in an amount as described for the premix above. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

The relative amount of drug substance and surface modifier can vary widely and the optimal amount of the surface modifier can depend, for example, upon the particular drug substance and surface modifier selected, the critical micelle concentration of the surface modifier if it forms micelles, etc. The surface modifier preferably is present in an amount of about 0.1–10 mg per square meter surface area of the drug substance. The surface modifier can be present in an amount of 0.1–90%, preferably 20–60% by weight based on the total weight of the dry particle.

Pharmaceutical compositions according to this invention include the particles described above and a pharmaceutically acceptable carrier therefor. Suitable pharmaceutically acceptable carriers are well known to those skilled in the art. These include non-toxic physiologically acceptable carrier, adjuvants or vehicles for parenteral injection, for oral administration in solid or liquid form, for rectal administration, and the like. A method of treating a mammal in accordance with this invention comprises the step of administering to the mammal in need of treatment an effective amount of the above-described pharmaceutical composition. The selected dosage level of the drug substance for treatment is effective to obtain a desired therapeutic response for a particular composition and method of administration. The selected dosage level therefore, depends upon the particular drug substance, the desired therapeutic effect, on the route of administration, on the desired duration of treatment and other factors. As noted, it is a particularly advantageous feature that the pharmaceutical compositions of this invention exhibit unexpectedly high bioavailability as illustrated in the examples which follow. Furthermore, it is contemplated that the drug particles of this invention provide more rapid onset of drug action and decreased gastrointestinal irritancy.

It is contemplated that the pharmaceutical compositions of this invention will be particularly useful in oral and parenteral, including intravenous, administration applications. It is expected that poorly water soluble drug substances, which prior to this invention, could not have been administered intravenously, may be administered safely in accordance with this invention. Additionally, drug substances which could not have been administered orally due to poor bioavailability may be effectively administered in accordance with this invention.

The following example further illustrates the invention.

EXAMPLE 1

One phenytoin nanoparticulate dispersion was prepared using the prior art method of depyrogenating the grinding media, milling with surfactant and autoclaving and a phenytoin nanoparticulate dispersion was prepared according to this invention wherein the autoclaving of the drug was done prior to milling. The prior art process was as follows:

1. A sterile UB2 hood was cleaned with 70% alcohol and a sample of phenytoin was provided.

2. A Pyrex bottle was rinsed with water for injection (WFI) and allowed to air dry and set in an oven at 100° C. for 15 minutes and allowed to cool. The bottle and cap and polyethylene liner were soaked in 10 N NaOH for several minutes. After several rinses in water and WFI they were allowed to dry and loaded into sterilizable pouches and autoclaved for 20 minutes at 121° C. 50 g of conditioned $ZrSiO_3$ beads were transferred into the bottle, the bottle was capped with aluminum foil and placed in a 240° C. oven overnight and then allowed to cool in a sterile hood.

The drug (phenytoin) was transferred to the depyrogenated containers. A surfactant solution comprising 2.5% PVP/0.05% methyl paraben/0.05% propyl paraben/0.1% potassium sorbate was sterile filtered through a 0.22 micron filter in an amount to give a final drug to surfactant ratio of 2:1. This was transferred to the compound from step 2. Milling was achieved by capping the bottle and rotating the bottle on the roller mill for several days. The particle size was determined by removing a small aliquot to a small cryogenic vial while in the sterile hood. The resulting nanodispersion was aseptically filtered through a pure, sterilized (121° C. for 20 minutes) 5 micron filter unit. The milled nanoparticles were then autoclaved at 121° C. for 20 minutes.

The dispersions were studied to determine the stability after autoclaving with several excipients (to stabilize the suspensions) before and after autoclaving. The phenytoin dispersions comprised 5% phenytoin, 2.5% polyvinylpyrrolidone, 15 k buffer (0.1M citric acid adjusted to pH of 5 with 0.1M NaOH; preservatives such as 0.05% methyl paraben, 0.1% potassium sorbate and 0.05% propyl paraben.

The following Table I shows that the stability of the nano-dispersion has unstabilized after autoclaving with or without the addition of excipients.

TABLE I

| % comp. | % surf. | milling days | Before autoclaving size (nm) | added excipients | After autoclaving size (nm) |
|---|---|---|---|---|---|
| 5% | 2.5% | 6 | 208 | none | 534 |
| 4.7% | 2.4% | " | " | .2% DOSS | 668 |
| 4.1% | 2.1% | " | " | .2% MG-PC | 617 |
| 4.1% | 2.1% | " | " | 10% PEG 400 | >3 micron |
| 3.5% | 1.8% | " | " | 10% polyethylene glycol/.1% DOSS | 809 |

The process of the invention was exactly the same as above except the autoclaving step of step 2 was done with the Phenytoin present before the milling step and the last autoclaving step was omitted. The results of this process indicated that the drug nanoparticles were acceptably stable.

The particle size and stability of the nanodispersion were evaluated in biological fluids by viewing the nanodispersion under the simulated gastric fluid and the simulated intestinal fluid to see if particles would agglomerate. The nanodispersion in both biological fluids were stable and no agglomerations were seen in the samples which were autoclaved prior to milling as opposed to those samples which were sterilized under the prior art process.

I claim:

1. A method of preparing sterilized nanoparticulate crystalline drug particles comprising the steps of:

1) providing a drug substance having a solubility in water of less than 10 mg/ml 2) depyrogenating rigid grinding media having an average particle size less than 3 mm at from 200° C. to 300° C. for from 6 to 20 hours 3) mixing the drug substance and rigid grinding media and autoclaving it from 100° C. to 150° C. for 10 to 50 minutes and 4) adding a surface modifier to the autoclaved drug substance and rigid grinding media to a dispersion medium and wet grinding the drug substance sufficiently to maintain an effective average particle size of less than 400 nm.

2. The method of claim 1 wherein the depyrogenation step is carried out at from 240° C. to 260° C.

3. The method of claim 2 wherein the depyrogenation step is carried out for 8 hours.

4. The method of claim 1 wherein the rigid grinding media is selected from the group consisting of zirconium silicate beads, zirconium oxide stabilized with magnesia and glass beads.

5. The method of claim 4 wherein the rigid grinding media is zirconium silicate.

6. The method of claim wherein the drug substance is selected from the group consisting of analgesics, anti-inflammatory agents, anthelmintics, antiarrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardia inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and bisphosphonates, prostaglandins, radio-pharmaceuticals, sex hormones, anti-allergic agents, stimulants and anoretics, sympathomimetics, thyroid agents, vasodilators and xanthines.

7. The method of claim 6 wherein the drug substance is Phenytoin.

8. The method of claim 1 wherein the autoclaving step is carried out at 121° C. for 20 minutes.

9. The method of claim 1 wherein the surface modifier is selected from the group consisting of gelatin, casein, lecithin (phosphatides), gum acacia, cholesterol, tragacanth, stearic acid, benzalkonium chloride, calcium stearate, glyceryl monostearate, cestostearl alcohol, cetamacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, and polyvinylpyrrolidone.

10. The method of claim 9 wherein the surface modifier is selected from the group consisting of polyvinylpyrrolidone, an ethylene oxide-propylene oxide block copolymer, lecithin, an alkyl aryl polyether sulfonate, gum acacia, sodium dodecylsulfate, and dioctylester of sodium sulfosuccinic acid.

11. The method of claim 10 wherein said surface modifier is polyvinylpyrrolidone.

12. The method of claim 1 wherein the dispersion medium is water.

13. A method of preparing a stable dispersion comprising adding the particles resulting from claim 1 to a liquid dispersion medium.

14. The method of claim 13 wherein the liquid dispersion medium is water.

* * * * *